United States Patent [19]

Blewett et al.

[11] 4,078,013
[45] Mar. 7, 1978

[54] OLEFIN METATHESIS CATALYSTS AND PROCESS UTILIZING SAME

[75] Inventors: Charles W. Blewett, Ft. Mitchell, Ky.; William R. Garrett, Jr., Cincinnati, Ohio

[73] Assignee: Emery Industries, Inc., Cincinnati, Ohio

[21] Appl. No.: 743,558

[22] Filed: Nov. 22, 1976

[51] Int. Cl.$^2$ ............................................ C07C 3/62
[52] U.S. Cl. .......................... 260/683 D; 252/429 B; 260/666 A; 260/668 R; 260/669 R
[58] Field of Search .......... 260/683 D, 666 A, 668 R, 260/669 R; 252/429 B

[56] References Cited

U.S. PATENT DOCUMENTS 3,778,385   12/1973   Zuech ............................. 252/429 B
3,790,543   2/1974   Lehnert et al. .................. 252/429 B

OTHER PUBLICATIONS

Ichikawa et al, Journal of Organic Chemistry, vol. 41, No. 15, pp. 2633–2635, 7-23-76.

Primary Examiner—Delbert E. Gantz
Assistant Examiner—C. E. Spresser
Attorney, Agent, or Firm—Gerald A. Baracka; John D. Rice

[57] ABSTRACT

Improved homogeneous metathesis catalysts are obtained by the use of a nitrogenous modifying agent with a tungsten compound and organotin compound. These modified catalyst systems used for olefin metathesis give significantly increased conversions and excellent product selectivity.

8 Claims, No Drawings

OLEFIN METATHESIS CATALYSTS AND PROCESS UTILIZING SAME

BACKGROUND OF THE INVENTION

Olefin metathesis reactions (also referred to as dismutation or disproportionation reactions) wherein an olefin is converted to a product having a higher or lower carbon number than the starting material are known. These reactions are of considerable interest because of the versatility of the reaction and the numerous olefinic hydrocarbons available from petrochemical souces which are suitable for use in the reaction to yield useful products. While both heterogeneous and homogeneous catalysts can be used for these reactions the heterogeneous catalysts generally require higher reaction temperatures and pressures and give lower selectivity, particularly when using higher olefins. For these reasons recent emphasis has been to the development of new and improved homogeneous catalyst systems.

Homogeneous catalysts presently known and available are largely based on tungsten and molybdenum compounds, such as tungsten hexachloride, molybdenum pentachloride or tungsten oxytetrachloride, in combination with an organometallic compound of Group 1a, 3a or 4a of the Periodic Table (Handbook of Chemistry and Physics, 56th Edition, 1975-76), most notably lithium, aluminum, germanium or tin. For example, British Patent No. 1,208,068 discloses a homogeneous disproportionation catalyst system of molybdenum pentachloride or tungsten hexachloride and an organometallic compound of germanium or tin. The preferred catalyst for the process is derived from tungsten hexachloride and tetra-n-butyl tin. A binary catalyst system of tungsten hexachloride and n-butyllithium is also described by J. Wang et al in the Journal of Organic Chemistry, Vol. 33, No. 10 (1968) at pages 3794-6. A tertiary catalyst system consisting of a tungsten or molybdenum salt, an organotin compound and a boron halide or its etherate is also disclosed in U.S. Pat. No. 3,901,866. These catalysts are employed to polymerize cyclopentene to obtain cis- and trans-polypentenamers. The dismutation of olefins in the homogeneous phase employing a catalyst of an alcoholate of molybdenum or tungsten and an organometallic reducing agent is described in U.S. Pat. No. 3,855,340.

It is possible with the known homogeneous catalyst systems to obtain high product selectivity, however, this is typically accompanied by low conversion of the olefin. When measures are taken to increase conversion there is typically a corresponding decrease in the product selectivity. Also, with the previously reported tungsen/organotin cocatalysts there is considerable inconsistency in the results obtained so that even when optimum molar ratios and reaction conditions are employed drastically different conversion and product selectivity can be obtained from run to run. These variations have generally been attributed to indefinable variations in the tungsten compound. For example, tungsten compounds obtained from different suppliers and manufactured to the same product specifications can give markedly different results. Also, variations are often noted with tungsten reagents which have been stored even for a short period of time following all of the recommended storage procedures. Especially in the case of tungsten hexachloride, widely divergent results are obtained with reagents obtained from different suppliers even though the products are, by all measurable standards, identical or when the reagent has been stored for a period of time even though all the prescribed storage precautions have been strictly adhered to. In practice it has not been possible to obtain consistently high conversion of α-olefins with high selectivity to the desired product using heretofore known tungsten/organotin homogeneous catalyst systems.

It would be extremely advantgeous therefore if it were possible to consistently obtain increased conversions with high product selectivity in α-olefin metathesis reactions employing a homogeneous catalyst sysem. It would be even more desirable if such metathesis reactions consistently gave conversions of 75% or higher with a selectivity of 95+% and if the catalyst could be obtained by simple modification of a tungsten/organotin cocatalyst with readily available and economical modifying agents. It would be even more advantageous if the improved catalysts and results were obtained without regard to the source and storage history of the tungsten compound. These and other desirable features are now fully realized with the modified homogeneous olefin metathesis catalysts which will be described more fully below.

SUMMARY OF THE INVENTION

We have now quite unexpectedly discovered improved homogeneous metathesis catalysts obtained by modifying a tungsten compound, such as tungsten hexachloride, and an organotin compound, such as tetrabutyl tin, with a nitrogenous compound which can be an amine or nitrogen heterocycle. Useful amines include primary, scondary and tertiary amines. Useful heterocyclic compounds contain a nitrogen atom in a five- or six-membered ring. In addition to significantly improving the conversion and product selectivity the modified catalysts of this invention also, quite unexpectedly, make it possible to obtain consistent results without regard to the source or storage history of the tungsten compound. This latter feature is particularly advantageous since it eliminates variations which have heretofore been observed using tungsten compounds from different suppliers or when it was necessary to store the tungsten reagent after the original containers had been opened. It is totally unexpected and surprising that much improved and highly effective homogeneous catalyst systems are obtained by modification with nitrogenous compounds. This is espcially so in view of the report by V. M. especially et al in the Journal of Organic Chemistry, Vol. 36, No. 20 (1971), pp. 2951-2953, that pyridine greatly reduces the metathesis activity of a tungsten hexachloride/ethylaluminum dichloride catalyst system and the article by K. Ichikawa et al, Journal of Organic Chemistry, Vol. 41, No. 15 (1976), pp. 2633-2635, that tri-n-butylamine is not an effective additive for the $WCl_6/Bu_4Sn$ catalyzed metathesis of 1-octene.

The improved catalysts of this invention consist of a tungsten component, such as a tungsten halide or tungsten oxyhalide, and an organotin compound which is preferably a tetraalkyl tin compound wherein the alkyl groups contain from 1 to 8 carbon atoms. The molar ratio of organotin compound to tungsten compound will range from about 0.4:1 to 1.5:1. Especially useful modified catalysts are obtained using tungsten hexachloride or tungsten oxytetrachloride at a mole ratio (tin compound:tungsten component) of 0.9:1 to 1.1:1. The nitrogenous modifying agent can be an aliphatic amine, cycloaliphatic amine, aromatic amine or heterocyclic amine wherein the nitrogen atom is contained in a five- or six-membered ring. Secondary and tertiary aliphatic amines where the alkyl groups have from 1 to 8 carbon atoms, pyridine, piperidine and pyrrolidine are especially useful modifying agents for this invention particularly when the molar ratio of modifier to tungsten compound ranges from 0.25:1 to 0.75:1. The homogeneous modified catalysts find general application for all olefin metathesis reactions. They can be used to metathesize both internal and terminal olefinic materials containing up to about 50 carbon atoms. The catalysts are especially useful for the metathesis of α-olefins or mixtures of α-olefins containing 1 to 30 carbon atoms and, more preferably, 4 to 16 carbon atoms. The catalysts is employed in an amount such that from about 0.0003 mole to about 0.1 mole of the tungsten component is present per mole of the olefin.

DETAILED DESCRIPTION

The present invention relates to improved olefin metathesis catalysts and to processes utilizing these catalysts. In general, the modified catalysts of this invention are useful in a wide variety of metathesis reactions but they are most useful in reactions employing olefinic hydrocarbons of the general formula

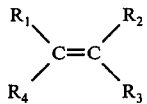

where $R_1$ is an alkyl group containing from 1 to 40 carbon atoms, a cycloalkyl or alkyl-substituted cycloalkyl group containing 3 to 20 carbon atoms, phenyl, a $C_{1-20}$ alkyl-substituted phenyl radical or radical of the formula

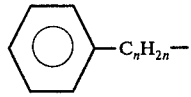

where $n$ is an integer from 1 to 20 and $R_2$, $R_3$ and $R_4$ are, independently, hydrogen or a radical as defined for $R_1$ such that the total number of carbon atoms does not exceed about 50. A pure olefin may be employed or a mixture of the same or different types of olefins can be used with the catalysts of this invention.

The modified homogeneous catalysts find particular applicability in processes where an α-olefin or mixture of α-olefins are metathesized. These α-olefins are readily available from petrochemmical sources and have the general formula $$R_5HC=CH_2$$

where $R_5$ is an alkyl group having from 1 to 30 carbon atoms and, more preferably, 4 to 16 carbon atoms. Suitable α-olefins of the above type include but are not limited to propylene, 1-butene, 1-pentene, 1-hexene, 1-octene, 1-nonene, 1-decene, 1-dodecene, 1-tetradecene and the like. The metathesis of 1-decene, for example, would yield 9-octadecene and can be depicted as follows:

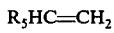
$$CH_3(CH_2)_7CH=CH_2 + CH_3(CH_2)_7CH=CH_2 \rightarrow CH_3(CH_2)_7CH=CH(CH_2)_7CH_3 + CH_2=CH_2$$

Where a mixture of αolefins is employed, such as with a 50/50 mixture of 1-octene and 1-decene, cross metathesis would occur in accordance with the equation:

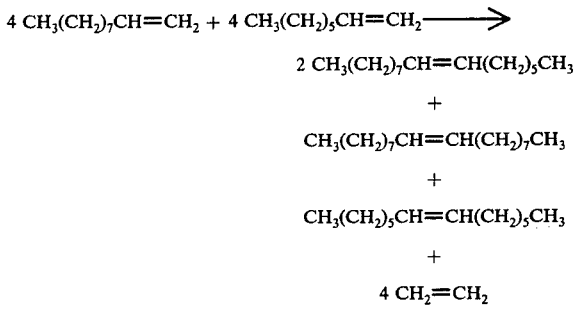

The present improved catalysts consist of a tungsten component and organotin component modified with an amine or heterocyclic compound having a nitrogen atom in the ring. Useful tungsten compunds include tungsten halides, tungsten oxyhalides and mixtures thereof. The halogen is preferably chlorine but can also be bromine, iodine or fluorine. Useful tungsten halides and oxyhalides include tungsten hexachloride, tungsten hexafluoride, tungsten hexabromide, tungsten pentachloride, tungsten pentabromide, tungsten tetrachloride, tungsten tetrabromide, tungsten oxytetrachloride, tungsten oxytetrabromide, tungsten dioxydibromide and the like. Tungsten hexachloride and tungsten oxytetrachloride are particularly useful for the preparation of improved catalysts of this invention because of their availability and the efficiency of the catalysts obtained therewith.

The organotin compound will correspond to the general formula

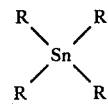

where R is an alkyl group containing from 1 to 16 carbon atoms, a cycloalkyl group containing from 3 to 8carbon atoms, benzyl, phenyl or an alkyl-substituted phenyl group containing from 7 to 12 carbon atoms. Suitable organotin compounds of the above type include tetramethyl tin, dimethyldiethyl tin, tetraethyl tin, diethyldibutyl tin, tetrabutyl tin, tetraoctyl tin, tetranonyl tin, tetracyclohexyl tin, tetrabenzyl tin, tetraphenyl tin and the like. Especially useful organotin compounds for the preparation of the modified catalyst systems of this invention are tetraalkyl tin compounds wherein the alkyl group contains from 1 to 8 carbon atoms. In terms of the above formula R would be a $C_{1-8}$ alkyl group. The molar ratio of the organotin compound to the tungsten compound can range from about 0.4:1 to 1.5:1, however, it is preferred that 0.8 to 1.2 moles organotin compound per mole tungsten compound be used. Especially useful homogeneous catalyst systems of this invention which give markedly superior results are obtained using tetra($C_{1-8}$ alkyl) tin compounds with tungsten hexachloride or tungsten oxytetrachloride at a mole ratio (tin compound:tungsten component) of 0.9:1 to 1.1:1.

A nitrogenous modifying agent is employed with the tungsten compound and organotin compound to obtain the improved homogeneous metathesis catalysts. The nitrogenous modifying agent may be an aliphatic amine, cycloaliphatic amine, aromatic amine or heterocyclic amine, that is, a compound wherein the nitrogen atom is contained in a five- or six-membered ring.

Useful secondary and tertiary aliphatic, cycloaliphatic or aromatic amines correspond to the general formula

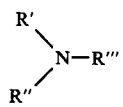

wherein R' and R" are, independently, an alkyl radical, branched or straight-chain, containing from 1 to 20 carbon atoms, a cycloalkyl radical containing from 3 to 8 carbon atoms, phenyl or alkyl-substituted phenyl radical wherein the alkyl substituent(s) contain(s) 1 to 8 carbon atoms and benzyl or other aralkyl radicals containing 8 to 20 carbon atoms and R''' is hydrogen or a radical as defined for R' and R". Secondary and tertiary amines wherein R', R" and R''' are $C_{1-8}$ alkyl, cyclohexyl, phenyl or benzl are espcially useful modifiers. Typical amine modifiers of this type include but are not limited to the dimethylamine, trimethylamine, diethylamine, triethylamine, dipropylamine, tripropylamine, diisopropylamine, dibutylamine, tributylamine, diisobutylamine, dicyclohexylamine, bis(1,3-dimethylbutyl) amine, bis(2-ethylhexyl)amine, didodecylamine, tridodecylamine, ditetradecylamine, dihexadecylamine, dioctadecylamine, dimethylethylamine, dimethylbenzylamine, dimethylcyclohexylaine, diethylmethylamine, diethylcyclohexylamine, N,N-dimethylaniline, N-benzyl-N-methylaniline and the like. Primary amines while not as effective as the secondary and tertiary aines can also be used to enhance the catalytic activity of the tungsten/organotin cocatalysts. Primary amines which can be used include methylamine, ethylamine, n-propylamine, isopropylamine, n-butylamine, 2-methylpropylamine, cyclohexylamine, 1,1-dimethylethylamine, 1,3-dimethylbutylamine, 2-amino-4-methylhexane, 1,4-dimethylpentylamine, 2-ethylhexylamine, 1,1,3,3-tetramethylbutylamine, dodecylamine, cyclopropylamine, aniline, benzylamine, α-phenylethylamine and the like.

In addition to the aliphatic, cycloaliphatic and aromatic amines mentioned above, heterocyclic amines wherein the nitrogen atom is contained in a five- or six-memberd ring are also useful modifiers for this invention. These heterocyclic amine modifying agents correspond to the general formula

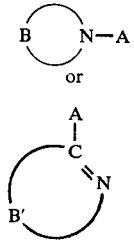

where A is hydrogen or a radical the same as defined above for R' and B and B' are bivalent radicals, saturated or containing unsaturation, such that a five- or six-membered hetereocyclic ring is formed. Preferred heterocyclic amines corresponding to formulwa I are those wherein A is hydrogen or a methyl group and the radical B is a bivalent saturated or unsaturated $C_4$ or $C_5$ hydrocarbon radical which may have from 1 to 5 alkyl groups containing 1 to 3 carbon atoms each replacing the available hydrogen atoms. Especially useful heterocyclic amines of type I are those where B is a bivalent hydrocarbon radical of the formula —$C_4H_8$—, —$C_4H_6$—, —$C_4H_4$—, —$C_5H_{10}$—, —$C_5H_8$—, —$C_5H_6$—, or any of these radicals wherein one or more of the hydrogen atoms is replaced with a methyl group with the proviso that no carbon atom in the ring contains more than one methyl group. As will be obvious to those skilled in the art, numerous position isomers are possible when hydrogen atoms are replaced by methyl radicals and all of these isomers are within the scope of the above definition. Preferred heterocyclic amine modifiers of formula II are those wherein A is a hydrogen or methyl group and the radical B' is a bivalent saturated or unsaturated $C_3$ or $C_4$ hydrocarbon radical which can have from 1 to 4 alkyl groups containing from 1 to 3 carbon atoms each replacing the available hydrogens. Especially useful modifiers of type II are those where B' is bivalent hydrocarbon radical of the formula —$C_4H_8$—, —$C_4H_6$—, —$C_4H_4$—, —$C_3H_6$—, —$C_3H_4$— or any of these radicals having one or more of the hydrogen atoms replaced with a methyl group with the proviso that no carbon atom in the ring will contain more than one methyl group.

Illustrative five- and six-membered heterocyclic compounds of the above types which can be employed in accordance with the present invention are pyridine, α-picoline, β-picoline, γ-picoline, 1:2-dihydropyridine, 1:4-dihydropyridine, 2:3-dihydropyridine, 2:5-dihydropyridine, 3:4-dihydropyridine, 1:2:3:4-tetrahydropyridine, 1:2:3:6-tetrahydropyridine, 2:3:4:5-tetrahydropyridine, the dimethylpyridines (lutidines), the trimethylpyridines (collidines), piperdine, N-methylpiperidine, 1-methylpiperidine, 2-methylpiperidine, 3-methylpiperidine, pyrrolidine, N-methylpyrrolidine, 1-methylpyrrolidine, 2-methylpyrrolidine, pentamethylpyrrolenine, and the like.

In addition to the above-described aliphatic, cycloaliphatic, aromatic and heterocyclic amines which are especially useful for this invention numerous other nitrogenous compounds incorporating the above structural elements can advantageously be employed to modify the tungsen/organotin catalysts. Such compounds include diamines and polyamines such as ethylenediamine, hexamethylenediamine, o-, m- and P-phenylenediamine, p,p'-diaminobipenyl, diethylenetriamine, tetraethylenepentamine, and other heterocyclic compounds such as pyrid-2-one, pyrid-3-one, piperid-2-one, piperid-3-one, inolde, skatole, quinucilidine, quinoline, tetrahydroquinoline, acridine, phenanthridine, isoquinoline, pyridazine, pyrimidine, pyrazine, cinnoline, phthalazine, quinazoline, phenazine, hexamethylenetetramine, triazines, oxindole, indoxyl, oxazole, thiazle, and the like.

The molar ratio of the amine modifier to the tungsen compound will range from about 0.1:1 to 0.95:1, howver, it is especially useful if about 0.25 to 0.75 moles amine modifier be used per mole of the tungsten compound. Especially effective homogeneous catalysts are obtained using pyridine, piperidine, pyrrolidine or a secondary or tertiary aliphatic amine wherein the alkyl groups contain from 1 to 8 carbon atoms with tungsten hexachloride or tungsten oxytetrachlorie and a tetra ($C_{1-8}$ alkyl) tin compound. Such catalysts are particularly effective for the metathesis of α-olefins and make it possible to consistently obtain conversions greater than 75% with 95+% selectivity.

To conduct metathesis reactions employing the modified and improved catalysts of this invention a wide variety of reaction conditions can be employed. In general, the reaction conditions are the same as those described in the prior art and reference may be had thereto for more details. Operating temperatures can vary over a wide range from about 0° C to about 220° C, however, the reaction is most generally conducted at a temperature of about 50° C to 150° C. The reaction can be conducted in the presence or absence of an inert hydrocarbon diluent such as benzene, toluene, xylene or the like. Paraffinic and cycloparaffin hydrocarbons such as cyclohexane, methylcyclohexane, pentane, hexane, isooctane and the like can also be used for this purpose. While it may sometimes be advantageous to use diluents with high melting olefins or olefin mixtures, diluents are not necessary. The metathesis reaction can be conducted over a wide range of operating pressures varying from subatmospheric to superatmospheric. The pressure will generally be governed by the particular olefin or olefin mixture used and other operating conditions. While operating pressures can range up to five atmospheres or higher, whenever possible the reaction is conducted at atmospheric pressure or as close thereto as feasible, especially when metathesizing $\alpha$olefins, since this facilitates removal of ethylene which drives the reaction. The reaction is generally conducted under an inert atmosphere of nitrogen, argon or helium and precautions are taken to exclude moisture from the system. Using these reaction conditions it is possible to consistently obtain conversions of 75% or higher with a selectivity of 95+% and to minimize, and in some cases completely eliminate, variations due to the origin of the tungsten component.

The modified catalysts of this invention are extremely effective when employed in methathesis reactions even at very low levels. High conversions of $\alpha$-olefins and high product selectivity are obtained when there is present an amount as low as 0.0003 mole tungsten component per mole of the olefin to be metathesized. While there is theoretically no upper limit to the amount of catalyst which can be used, there is generally no advantage in using amounts much greater than about 0.1 mole tungsten component per mole olefin. Most generally the tungsten component will range from about 0.0006 to about 0.05 mole per mole of the olefin, particularly when metathesizing $\alpha$-olefins.

In a typical batch laboratory preparation the desired amount of the tungsten compound is combined with the olefin to be metathesized in an inet atmosphere followed by the addition of the modifying agent. The organotin compound is then charged and the reactor and its contents heated to the desired temperature and pressurized, if desired. Samples are periodically removed from the reaction mixture and analyzed to follow the reaction.

Numerous modifications of this procedure are, however, possible. For example, the metathesis reaction can be conducted as a continuous or semi-continuous operation. Also, it is possible to add the catalyst components to the system as a solution in a suitable solvent. This procedure is particularly advantageous in continuous and semi-continuous operations since it facilitates handling and metering of the various catalyst components into the system. It is also possible to combine two or more of the catalyst components prior to combining with the olefin or prior to introduction into the reactor even though maximum catalyst efficiency appears to be obtained when the components are admixed and charged in the above-described step-wise manner. Still other modifications will be obvious to those skilled in the art and are within the scope of the present invention as will be evident from the following examples.

EXAMPLE I

Tungsten hexachloride 2.2 millimoles was weighed into a glass reactor under a nitrogen atmosphere and 3.50 moles 1-decene was added. The solution was stirred under nitrogen for about 15 minutes and 0.5 millimole N,N-dimethylaniline added followed by stirring for about five minutes and the addition of 2.2 millimoles tetrabutyl tin. The reaction mixture was then heated to 90° C while maintaining the nitrogen atmosphere. After 30 minutes a sample was removed from the reactor and chromatographic analysis indicated 75.6% conversion of the 1-decene with 99.0% selectivity to the desired 9-octadecene. By continuing the reaction at 90° C for an additional 30 minutes the conversion was increased to 83.0% without decreasing the selectivity. The reaction temperature was then increased to 175° C and after 3½ hours (total reaction time) 85.1% conversion with 98.5% selectivity was obtained.

EXAMPLE II

Following the procedure described in Example I, 1-decene (5.25 moles) was metathesized to 9-octadecene. The catalyst consisted of 2.2 millimoles tungsten hexachloride and 2.2 millimoles tetrabutyl tin modified with 0.5 millimole pyridine. After one hour at 90° C the conversion was 79% with 99% selectivity of the desired 9-octadecene. By increasing the reaction temperature to 150° C and continuing the reaction for an additional 2½ hours the conversion was increased to 87% while maintaining the high selectivity (97%).

EXAMPLE III

Example II was repeated except the amount of 1-decene was reduced to 1.75 moles. After only 30 minutes reaction at 90° C the conversion was 84% with 99% selectivity to the 9-octadecene. With additional heating the conversion was increased to greater than 90% with 98% selectivity.

EXAMPLE IV

In a manner similar to that described in Example I 1-octene was methatesized to produce 7-tetradecene. For this reaction, 3.50 moles freshly distilled 1-octene was combined with 2.2 millimoles tungsten hexachloride followed by the addition of 0.5 millimole pyridine and 2.2 millimoles tetrabutyl tin. The temperature of reaction was 90° C. Conversion of 1-octene and selectivity to the 7-tetradecene was followed by chromatographic analysis of samples taken at 30, 60 and 150 minute intervals with the following results:

| Reaction Time: | % conversion | % Selectivity |
|---|---|---|
| 30 minutes | 78 | 99 |
| 60 minutes | 80 | 99 |
| 150 minutes | 82 | 99 |

EXAMPLES V-VIII

Several metathesis reactions were conducted to demonstrate the use of additional heterocyclic amine modifiers with the tungsten hexachloride/tetrabutyl tin cocatalyst. For each of these experiments 3.5 moles 1-decene was was used with 2.2 millimoles tungsten hexachlorie and 2.2 millimoles tetrabutyl tin. The reactions were all conducted at 90° C. The amount and type of heterocyclic modifier are set forth below with results obtained for each.

| Modifier (Millimoles) | Reaction Time (Minutes) | Conversion (Percent) | Selectivity (Percent) |
|---|---|---|---|
| Pyrrolidine (0.5) | 30 | 70 | 99 |
| Pyrrolidine (1.1) | 30 | 75 | 99 |
| | 240 | 88 | 98 |
| 4-Picoline (0.5) | 30 | 72 | 98 |
| | 60 | 78 | 99 |
| Piperidine (0.5) | 30 | 76 | 98 |
| | 60 | 78 | 99 |
| | 120 | 81 | 99 |

EXAMPLE IX

A tungsten/organotin cocatalyst system was modified with N,N-dimethylbenzylamine. The catalyst was prepared by combining 2.2 millimoles tungsten hexachloride in 3.5 moles 1-decene followed by addition of 0.5 millimole N,N-dimethylbenzylamine and 2.2 millimoles tetrabutyl tin. The reaction mixture was then heated at 90° C and the metathesis was followed by chromatographic analysis of samples removed at 30 minute intervals. After the first 30 minutes reaction 68% conversion and 97% selectivity was obtained. The conversion was increased to 77% without lowering the selectivity upon heating an additional 60 minutes.

EXAMPLE X n-Butylamine (0.57 millimole) was used as the modifying agent with 2.3 millimoles tungsten hexachloride and 2.3 millimoles tetrabutyl tin. The modified homogeneous catalyst was prepared in the usual manner and employed for the metathesis of 1-octene. 72% Conversion of the olefin was achieved with 98.2% selectivity after 30 minutes. The conversion was increased to 78% when the reaction was continued for an additional sixty minutes without any significant (<0.2%) reduction in selectivity.

EXAMPLES XI–XIV

To demonstrate the effect of varying the amount of the modifier the following experiments were conducted in accordance with the procedure of Example I except that the modifying agent was pyridine. The molar ratio of the tetrabutyl tin to tungsten hexachloride was 1:1 for all of these runs, however, the ratio of pyridine to tungsten hexachloride ranged from 0.167:1 up to 0.5:1. The metathesis reactions were conducted at 90° C and the following results were obtained:

| Molar ratio (pyridine:WCl$_6$) | Reaction Time (Minutes) | Conversion (%) | Selectivity (%) |
|---|---|---|---|
| 0.167:1 | 30 | 58 | 99 |
| | 180 | 70 | 98 |
| 0.25:1 | 30 | 70 | 98 |
| | 60 | 80 | 98 |
| 0.377:1 | 30 | 80 | 99 |
| | 290 | 88 | 99 |
| 0.50:1 | 30 | 65 | 99 |
| | 60 | 83 | 99 |
| | 100 | 87 | 98 |

Increasing the molar ratio of the pyridine to tungsten hexachloride to 0.75 required an increase in the reaction temperature to obtain acceptable conversions, however, the selectivity of these reactions remained very high. For example, after 2½ hours at 175° C 70% conversion of the 1-decene with 99% selectivity was achieved. Ninety percent conversion was obtained at 185° C after 5 hours reaction with 98% selectivity to the desired 9-octadecene. No reaction was obtained when the molar ratio was further increased to 1:1.

EXAMPLE XV

To demonstrate the marked improvement obtained with the modified homogeneous metathesis catalysts of this invention a direct comparison was made employing a modified and unmodified tungsten hexachloride/tetrabutyl tin cocatalyst system.

A. 1-Decene was combined with 2.2 millimoles freshly opened reagent grade tunsten hexachloride (Research Organic/Inorganic Chem. Corp. 99% $WCl_6$) and 2.2 millimoles tetrabutyl tin and the reaction mixture heated to 90° C. The conversion and selectivity were determined after 30, 90 and 150 minutes and the following results were obtained:

| Reaction time: | % Conversion | % Selectivity |
|---|---|---|
| 30 minutes | 18 | 99 |
| 90 minutes | 21 | 99 |
| 150 minutes | 21 | 99 |

B. The experiment was repeated using the same amount of 1-decene, tungsten hexachloride and tetrabutyl tin except that for this reaction 0.5 millimole pyridine was added after the tungsten hexachloride and before charging the tetrabutyl tin. The results obtained at 90° C with the pyridine modified catalyst were as follows:

| Reaction Time: | % Conversion | % Selectivity |
|---|---|---|
| 30 minutes | 52 | 99 |
| 90 minutes | 81 | 99 |
| 150 minutes | 85 | 99 |

It is evident from the above data that under the same conditions (90° C) much improved conversion of the 1-decene can be obtained using the modified catalysts of this invention without adversely affecting the product selectivity. 83% Conversion is obtained within 60 minutes with 99% selectivity when the pyridine is increased to 1.1 millimoles. Similar improved results are observed using pyridine and other amine modifiers when the tungsten compound is tungsten oxytetrachloride and the organotin compound is tetraoctyl tin.

EXAMPLE XVI

Tungsten oxytetrachloride (1.0 millimole) was combined with 3.14 moles 1-decene under an inert atmosphere. Pyridine (0.26 millimole) and tetrabutyl tin (1.0 millimole) were then charged to the reactor and the mixture heated to 90° C with agitation. After one hour 81% conversion of the 1-decene was obtained with 98.4% selectivity to the desired 9-octadecene.

EXAMPLE XVII

7-Tetradecene and 9-octadecene were cross-metathesized employing a homogeneous modified catalyst. For the reaction, 1 mole 7-tetradecene and 1 mole 9-octadecene were combined in the reactor with 12.9 millimoles tungsten hexachloride. Pyridine (6.5 millimoles) was charged to the reactor followed by the addition of 12.9 millimoles tetrabutyl tin. The reaction was conducted at 90° C and after 30 minutes reaction, near equilibrium conversion of the olefins was obtained with high selectivity to the equilibrium mixture of 1 part 7-tetradecene, 1 part 9-octadecene and 2 parts 7-hexadecene. When the experiment was repeated in an identical manner but using an unmodified catalyst (12.9 millimoles tungsten hexachloride with 12.9 millimoles tetrabutyl tin) conversion of the olefins was significantly greater than the theoretical equilibrium conversion due to the lower selectivity of the reaction to the desired cross-methathesized products.

EXAMPLE XVIII

To demonstrate the ability of the modified catalysts to minimize variances which result from the storage history of the tungsten component the following comparative experiments were conducted. For these experiments both modified and unmodified catalysts were prepared using (a) freshly opened reagent grade tungsten hexachloride (Atomergic Chemetals Co., 99% $WCl_6$) and (b) the same tungsten hexachloride which had been stored in the original container under strictly anhydrous conditions for more than 10 months. The resulting catalysts were then evaluated for their ability to metathesize 1-decene to 9-octadecene at 90° C. Experimental details were as follows:

A. 3.5 Moles 1-decene was combined with 2.2 millimoles of the freshly opened tungsten hexachloride and 2.2 millimoles tetrabutyl tin. Results after 60 minutes reaction:
Conversion 59%
Selectivity 90%

B. 3.5 Moles 1-decene was combined with 2.2 millimoles tungsten hexachloride which had been stored for more than 10 months under strictly anhydrous conditions and 2.2 millimoles tetrabutyl tin. Results after 60 minutes reaction:
Conversion 28%
Selectivity 93%

C. 3.5 Moles 1-decene was combined in a step-wise manner with 2.2 millimoles of the freshly opened tungsten hexachloride, 1.1 millimole pyridine and 2.2 millimoles tetrabutyl tin. Results after 60 minutes reaction:
Conversion 83%
Selectivity 99%

D. 3.5 Moles 1-decene was combined in a stepwise manner with 2.2 millimoles tungsten hexachloride which had been stored for more than 10 minutes under strictly anhydrous conditions, 1.1 millimoles pyridine and 2.2 millimoles tetrabutyl tin. Results after 60 minutes reaction:
Conversion 83.5%
Selectivity 99%

The above data clearly demonstrates the advantage obtained with the pyridine modified catalysts. Whereas a marked decrease in catalyst efficiency was obtained using the unmodified catalyst prepared from the "aged" tungsten hexachloride there was no difference in the catalyst activity of the pyridine modified catalysts prepared using the "fresh" or "aged" tungsten hexachloride.

That widely divergent results can be obtained with unmodified cocatalysts prepared using tungsten hexachloride obtained from different sources is also evident by a comparison of the results obtained in the above-described run (A) with the results of Example XV(A). The unmodified catalysts employed for these experiments were identical in all respects except the tungsten reagents were obtained from different suppliers. Even though both reagents had the same analysis, when the unmodified catalysts prepared therefrom were evaluated in identical metathesis reactions there was a marked disparity in catalyst efficiency. On the other hand, when pyridine modified catalysts were prepared in accordance with this invention using these same two tungsten reagents and when these modified catalysts were evaluated (run (C) of this Example and Example XV (B) for the metathesis of 1-decene both modified catalysts gave excellent results and no appreciable difference in catalytic activity could be detected. Both modified catalysts gave greater than 80% conversion of the olefin within 60 minutes with 99% selectivity to 9-octadecene.

We claim:
1. A process for metathesizing olefins which comprises contacting an olefin of the general formula

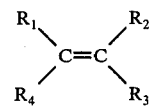

where $R_1$ is an alkyl group containing from 1 to 40 carbon atoms, a cycloalkyl or alkyl-substituted cycloalkyl group containing 3 to 20 carbon atoms, phenyl, a $C_{1-20}$ alkyl-substituted phenyl radical or radical of the formula

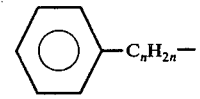

where n is an integer from 1 to 20 and $R_2$, $R_3$ and $R_4$ are, independently, hydrogen or a radical as defined for $R_1$ such that the total number of carbon atoms in the olefin does not exceed about 50, with a homogeneous catalyst at a temperature from about 0° to about 220° C under substantially anhydrous conditions, said homogeneous catalyst consisting essentially of:
 a. a tungsten halide or tungsten oxyhalide;
 b. an organotin compound of the formula

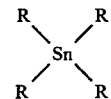

where R is an alkyl group containing from 1 to 16 carbon atoms, a cycloalkyl group containing from 3 to 8 carbon atoms, benzyl, phenyl or an alkyl-substituted phenyl group having from 7 to 12 carbon atoms; and
 c. a nitrogenous modifying agent selected from the group consisting of aliphatic amines, cycloaliphatic amines, aromatic amines and heterocyclic amines wherein the nitrogen is contained in a five- or six-membered ring, the molar ratio of (b) to (a) ranging from 0.4:1 to 1.5:1 and the molar ratio of (c) to (a) ranging from 0.1:1 to 0.95:1, said catalyst employed in an amount so that from about 0.0003 mole to about 0.1 mole of (a) is present per mole of the olefin.

2. The process of claim 1 conducted at a temperature in the range 50° C to 150° C and wherein the olefin is an α-olefin or mixture of α-olefins and from about 0.0006 mole to about 0.05 mole (a) is present per mole α-olefin.

3. The process of claim 1 wherein (a) is tungsten hexachloride or tungsten oxytetrachloride, (b) is a tetraalkyl tin compound wherein the alkyl groups contain from 1 to 8 carbon atoms, (c) corresponds to a compound of the formula

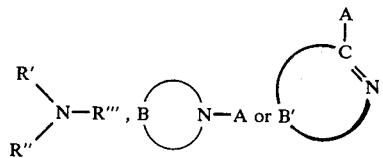

where R' and R" are an alkyl radical having from 1 to 20 carbon atoms, a cycloalkyl group having from 3 to 8 carbon atoms, phenyl, a $C_{1-8}$ alkylsubstituted phenyl radical, benzyl or an aralkyl radical containing 8 to 20 carbon atoms, R''' is hydrogen or a radical as defined for R', A is hydrogen or a radical as defined for R', B is a bivalent radical of the formula $—C_4H_8—$, $—C_4H_6—$, $C_4H_4—$, $C_5H_{10}—$, $—C_5H_8—$, $—C_5H_6—$ or any of these radicals wherein one or more of the hydrogen atoms is replaced with a methyl group with the proviso that no carbon atom in the ring contains more than one methyl group, B' is a bivalent radical of the formula $—C_4H_8—$, $—C_4H_6—$, $—C_4H_4—$, $—C_3H_6—$, $—C_3H_4$- or any of these radical wherein one or more of the hydrogen atoms is replaced with a methyl group with the proviso that no carbon atom in the ring contains more than one methyl group, the molar ratio of (b) to (a) ranges from about 0.8:1 to 1.2:1 and the molar ratio of (c) to (a) is between about 0.25:1 and 0.75:1.

4. The process of claim 3 wherein the olefin is an α-olefin or mixture of α-olefins of the general formula $R_5HC=CH_2$ wherein $R_5$ is an alkyl group having from 1 to 30 carbon atoms and the active catalyst specie is formed in situ by first combining the olefin with component (a), then adding the nitrogenous modifying agent (c) and finally component (b).

5. The process of claim 4 wherein (c) is pyridine, piperidine, pyrrolidine or a secondary or tertiary aliphatic amine wherein the alkyl groups contain from 1 to 8 carbon atoms and the molar ratio of (b) to (a) is between 0.9:1 and 1.1:1.

6. The process of claim 5 conducted at a temperature of 50° C to 150° C using about 0.0006 mole to 0.5 mole (a) per mole of the olefin.

7. The process of claim 6 wherein (a) is tungsten hexachloride, (b) is tetrabutyl tin and (c) is pyridine.

8. The process of claim 7 wherein the olefin is 1-decene or 1-octene.

* * * * *